United States Patent [19]

Kinoshita et al.

[11] Patent Number: 5,728,350
[45] Date of Patent: Mar. 17, 1998

[54] CHEMICAL OR MICROBIOLOGICAL TEST KIT

[75] Inventors: Yuichi Kinoshita; Fumio Tanaka, both of Chuo-Ku; Chie Shibuya, Shinjuku-Ku; Chizuko Ohshina, Shinjuku-Ku; Kiyoshi Oguchi, Shinjuku-Ku, all of Japan

[73] Assignee: Showa Yakuhin Kako Co., Ltd., Tokyo, Japan

[21] Appl. No.: 715,492

[22] Filed: Sep. 18, 1996

Related U.S. Application Data

[63] Continuation of Ser. No. 387,893, filed as PCT/JP93/01157, Aug. 19, 1993, published as WO94/04723, Mar. 3, 1994, abandoned.

[30] Foreign Application Priority Data

Aug. 21, 1992  [JP]  Japan ................... 4-222776

[51] Int. Cl.[6] ..................................... G01N 21/01
[52] U.S. Cl. ................... 422/61; 422/58; 436/809; 435/288.2
[58] Field of Search ................. 422/58, 61, 102; 436/808–810; 435/286.3, 288.2

[56] References Cited

U.S. PATENT DOCUMENTS

| | | | |
|---|---|---|---|
| 1,967,557 | 10/1934 | John | 422/61 |
| 3,497,320 | 2/1970 | Blackburn et al. | 422/61 |
| 3,992,158 | 11/1976 | Przyhylowicz et al. | 422/58 |
| 4,038,030 | 7/1977 | Albright et al. | 422/61 |
| 4,087,332 | 5/1978 | Hansen | 195/127 |
| 4,153,512 | 5/1979 | Messner et al. | 435/33 |
| 4,260,392 | 4/1981 | Lee | 23/230 |
| 4,818,677 | 4/1989 | Hoykaufman et al. | 422/58 |
| 4,898,529 | 2/1990 | Muchnik | 425/542 |
| 4,904,605 | 2/1990 | O'Brien et al. | 422/61 |
| 5,047,322 | 9/1991 | Emmons | 435/6 |

FOREIGN PATENT DOCUMENTS

| | | |
|---|---|---|
| 0 415 679 A2 | 3/1991 | European Pat. Off. |
| 50-145576 | 11/1975 | Japan |
| 50-38717 | 12/1975 | Japan |
| 52-154589 | 12/1977 | Japan |
| 53-21677 | 7/1978 | Japan |
| 55-44599 | 11/1980 | Japan |
| 58-209995 | 12/1983 | Japan |
| 60-222770 | 11/1985 | Japan |
| 61-96999 | 5/1986 | Japan |
| 62-103542 | 5/1987 | Japan |
| 62-182652 | 8/1987 | Japan |
| 63-219397 | 9/1988 | Japan |
| 3-49695 | 3/1991 | Japan |
| 3-61857 | 3/1991 | Japan |
| 3-282257 | 12/1991 | Japan |
| 4-18351 | 1/1992 | Japan |

OTHER PUBLICATIONS

Allen, et al., A Noninstrumented Quantitative Test System and Its Application for Determining Cholesterol Concentration in Whole Blood, *Clinical Chemistry*, vol. 36, No. 9, 1990, pp. 1591–1597.

Ploum et al., Test strip enzyme immunoassays and the fast screening of nortestosterone and clenbuterol residues in urine samples at the parts per billion level, *Journal of Chromatography*, 564 (1991), pp. 413–427.

Zhujun et al., Poly(vinyl alcohol) as a Substrate for Indicator Immobilization for Fiber–Optic Chemical Sensors, *Analytical Chemistry*, vol. 61, No. 3, 1989, pp. 202–205.

*Primary Examiner*—Lyle A. Alexander
*Attorney, Agent, or Firm*—Cushman Darby & Cushman IP Group of Pillsbury Madison & Sutro LLP

[57] ABSTRACT

A test kit for a chemical test or microbiological test, which comprises at least one independent sample-receiving part on a support is disclosed. The test kit of the present invention is usable for various chemical and microbiological tests which have been conducted with a plastic microplate and which have necessitated many reaction and culture steps in the prior art. The test kit of the present invention can be produced at an extremely low cost because of its structure. The test kit can previously contain a reagent necessitated for the test to remarkably facilitate the test.

13 Claims, 5 Drawing Sheets

CHEMICAL OR MICROBIOLOGICAL TEST KIT

This is a continuation of application Ser. No. 08/387,893, filed Feb. 21, 1995, which was abandoned upon the filing hereof; which was a National Phase of PCT/JP93/01157, filed Aug. 19, 1993 published as WO94/04723, Mar. 3, 1994.

TECHNICAL FIELD

The present invention relates to a test kit usable for a chemical or microbiological test, particularly for the determination of antimicrobial susceptibility by a microdilution broth method.

BACKGROUND ART

A plastic microplate having wells is usually used as a reaction or culture vessel in a chemical test comprising a step of reacting a chemical sample with a reagent or in a microbiological test comprising a step of culturing a microorganism in a sample, particularly in a test wherein many samples are treated, the sample is reacted with various reagents or the culture must be conducted in various systems.

For example, a plastic plate having many small wells is generally used in an immunological test such as ELISA. In the determination of the antimicrobial susceptibility, namely determination of the minimum inhibitory concentration (MIC), by the microdilution broth method, a conventional single disc method comprising an agar plate dilution or agar diffusion is further improved by saving lavor and also by automation. The MIC determination method by the microdilution broth method was standardized by Nippon Kagaku Ryoho Gakkai (Japan Chemotherapy Society) in 1989. In this method, the use of the same microplate having U-shaped wells as that used in an immunological test is suggested.

In a test wherein such a microplate is used, each reaction or culture of a microorganism is conducted in a different well of the plate. For example, in the MIC determination by the microdilution broth method wherein such a microplate is used, an antibacterial drug of varied concentrations is fed into each well, and the growth of the bacteria in each well is observed to determine the minimum inhibitory concentration. For such a test, a microplate prepared by pouring given amounts of the antibacterial drug into the wells thereof and drying the plate or freeze-storing thereof has been put on the market. However, inexpensive microplates is not available on the market, since the cost of the microplates per se is high. Under these circumstances, it is eagerly demanded by users to lower the cost.

Therefore, the object of the present invention is to provide an inexpensive test kit usable for a chemical test or microbiological test in which the reaction or culture in various ways with a relatively small amount of a sample is necessitated as described above.

DISCLOSURE OF THE INVENTION

The inventors have noticed that the concept of the test kit is not to be restricted to that of conventional test kits such as the above-described microplates, that the function of such a test kit is to efficiently retain the numerous independent reaction systems or culture systems and that it is enough to only satisfy such a function. After intensive investigations, the inventors have found that the object of the invention can be attained with a test kit comprising a support and small parts arranged and fixed thereon, which are capable of receiving the reaction system or culture system. The present invention has been completed on the basis of this finding.

Thus, the present invention provides a test kit for a chemical or microbiological test, which comprises a support and one or more independent sample-receiving parts formed thereon.

Namely, in the test kit of the present invention, an aqueous or hydrophilic reaction system, culture system or the like is kept by the water-absorbing, hydrophilic and water-retaining properties or the like of the small parts formed on the support unlike in the above-described microplate wherein the reaction or culture system is kept in wells. Thus by forming independent sample-receiving parts on the support, the same function as that of the microplate having wells can be obtained. In the actual test, a reaction or culture system to be tested is retained in the sample-receiving parts and the progress of the reaction or growth of a microorganism is detected by ordinary method to obtain the test results.

In the test kit of the present invention, the reaction system or culture system can be retained mainly inside the sample-receiving part by absorption or it can be kept in the form of drops on the sample-receiving parts.

The term "sample-receiving part" herein has not only a limited means of "part for receiving only a sample to be tested" but also a part for retaining a reaction system or culture system used in an intended chemical or microbiological test.

The adjacent sample-receiving parts are independent and separated from each other, since when they are brought into contact with each other, the components in the reaction system or culture system retained therein will be mixed together. The materials for the support and the sample-receiving parts are selected so that the reaction or culture system kept in each sample-receiving part can be substantially kept in this part and does not escape therefrom in the course of the intended test.

In order to prevent the escape of the aqueous reaction system, culture system or the like retained in the sample-receiving part from this part to the outside through the support in the course of the test, the support must be prepared from a material having relatively high hydrophobic properties. However, when a material having a higher hydrophilic and water-retaining properties is used for forming the sample-receiving part, the above-described function can be assured even when the material having weaker hydrophobic properties is selected for the support. Therefore, the selection of the materials for the support and the sample-receiving part is relative in this respect.

Since the above-described function can be sufficiently obtained by suitably selecting the materials for the sample-receiving parts and the support, it is unnecessary to separate the sample-receiving parts from each other with a diaphragm or the like. Although the test kit of the present invention preferably comprises only the sample-receiving parts and the support from the viewpoint of providing a very simple test kit, a diaphragm which is different from the support may be provided between the sample-receiving parts so as to more surely separate the sample-receiving parts from one another or for the convenience of the steps of forming these parts on the support. The diaphragms can be integrally formed with the support from the same material as that of the support or, separately from the support by a printing technique which will be described below.

BRIEF DESCRIPTION OF DRAWINGS

In FIG. 9, a portion 14 for absorbing the sample is swollen by absorbing the sample.

BEST MODE FOR CARRYING OUT THE INVENTION

Figure 1:
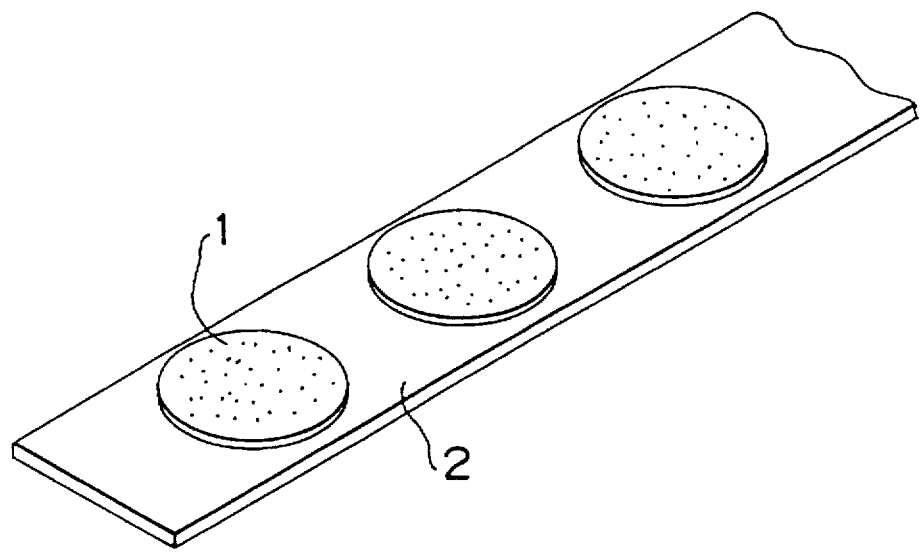
FIG. 1 is a partial rough perspective view of a test kit of the present invention produced in Example 1. The test kit of the present invention produced in Example 1 comprises sample-receiving parts 1 each composed of a pulp disc and an acrylic platy support 2.

The materials for the sample-receiving parts include, for example, fibers having water absorbing properties and water retentivity such as a filter paper and pulp discs; spongy porous polymer substances; polysaccharides such as starch, agar and pullulan; proteins such as casein and gelatin; cellulose derivatives such as crystalline cellulose, methylcellulose, ethylcellulose, carboxymethylcellulose, hydroxyethylcellulose and hydroxypropylcellulose; polymers such as polyvinyl alcohol, polyethylene glycol, polypropylene glycol, polyacrylamide, polyacrylic acid, sodium polyacrylate and polyvinylpyrrolidone as well as copolymers of them with another monomer according to the necessity; Paogen (a trade name of a product of Daiichi Kogyo Seiyaku Co., Ltd., which mainly comprises polyethylene glycol and polypropylene glycol) and partially crosslinked products thereof; natural sizes such as acacia gum, and mixtures of them.

Among them, polyvinylpyrrolidone, hydroxyethylcellulose, hydroxypropylcellulose, polyethylene glycol, polyvinyl alcohol and Paogen are preferred, since they have an excellent effect of thickening the liquid sample when the sample is absorbed and, therefore, the sample retained in the sample-receiving part is thickened in the course of the use to retain the sample more firmly, and whereby it is preferable that the sample is difficultly removed during the handling.

In order to more firmly retain the sample as described above, it is more preferred to use a water-absorbing gel as the material for the sample-receiving part.

Examples of the water-absorbing gels preferably usable herein include a polyvinyl alcohol/polyacrylate gel, crosslinked polyacrylate gel, crosslinked polyvinyl alcohol gel, crosslinked polyethylene oxide gel, crosslinked polyacrylamide gel (such as crosslinked polydiethylacrylamide gel and crosslinked polyisopropylacrylamide gel), crosslinked polyvinylpyrrolidone gel and crosslinked Paogen gel. These water-absorbing gels are usable either singly or in the form of a mixture of them.

When such a water-absorbing gel is used as the material for forming the sample-receiving part, it is used in the form of a mixture with a suitable binder.

Materials usable as the suitable binder herein include, for example, hydrophobic resins (insoluble in water) such as an acrylic resin put on the market under a trade name of Dianal BR-Resin by Mitsubishi Rayon Co., Ltd., polyvinyl butyral, polyester resin, polyurethane resin, fluororesin, silicone resin and styrene/butadiene latex resin, and water-soluble and organic solvent-soluble (i.e. amphiphatic) resins such as polyvinylpyrrolidone and hydroxypropylcellulose. These binders are usable either singly or in the form of a mixture of them.

The size and shape of the sample-receiving parts and the arrangement of them on the support are not particularly limited. They can be suitably selected depending on the selected material for the sample-receiving parts and process for producing the test kit of the present invention so far as they can retain a reaction system or culture system in an amount necessitated to the intended test.

When a fibrous material such as a filter paper or a spongy porous substance is used, the sample-receiving part is capable of retaining a relatively large amount of the sample. The sample-receiving part is usually in a round form having a diameter of about 3 to 20 mm or a rectangular form having a side length of about 3 to 20 mm, and it has a thickness of about 0.5 to 3 mm. The quantity of the sample to be contained in each sample-receiving part is usually about 0.005 to 0.1 ml.

When the material is the polymer, water-absorbing gel or the like, the sample-receiving part can be easily and efficiently formed by a printing technique and very small sample-receiving parts can be easily formed. For example, very small sample-receiving parts each having an area of about 5 mm$^2$ and a distance between the adjacent sample-receiving parts of about 0.5 mm or less can be formed. The receiving part having a thickness of 0.01 to 500 μm as a dried layer can be formed by printing at once. The quantity of a sample to be retained in the sample-receiving part is usually about 5 to 100 μg.

The material for forming the support is preferably selected from among relatively hydrophobic materials so that the reaction system or the like does not escape from the sample-receiving part. The material can be selected from among, for example, polymers such as a polyethylene, polypropylene, ethylene/vinyl acetate copolymer, ethylene/vinyl alcohol copolymer, polystyrene, polyacrylate, polyvinyl chloride, polyvinyl alcohol, polyvinyl butyral, polyamide, polyester, polycarbonate, polyurethane, polyimide and triacetylcellulose; sheets and films of a metal such as aluminum or stainless steel; and papers laminated with such a polymer.

The size, thickness and shape of the support are not particularly limited. They can be selected depending on the size, number and shape of the sample-receiving parts to be formed thereon and the procedure of the test so that suitable handling properties of the selected material can be obtained. The support is usually preferably in a rectangular form. The support is, for example, in a rectangular form having a side length of 0.5 to 2 cm, or in another rectangular form having a length of 8 to 15 cm and the same width as the sample-receiving part, and the thickness of the support is usually about 0.1 to 2 mm. The support may be either flexible or not depending on the handling in the test.

The color, transparency, etc. of the sample-receiving part and the support can be suitably selected so that a change indicating the test results such as the propagation of bacteria and progress of a color reaction can be detected. For example, a transparent support, black support or the like is usable.

The simplest test kit of the present invention is composed of a support comprising a suitable material and having suitable size and shape, and a suitable number of sample-receiving parts comprising a suitable material and having suitable size and shape, the sample-receiving parts being suitably arranged and fixed with an adhesive on the support (Example 1 and FIG. 1).

When the above-described polymer or water-absorbing gel is used as the material for the sample-receiving part, the polymer or water-absorbing gel and, if necessary, a suitable binder are dissolved or dispersed in a suitable solvent, and the resultant solution or dispersion is applied to the support to form a coating of a desired shape or it is dropped on the substrate with a dispenser and then dried to obtain the test kit of the present invention.

More preferably, the test kit of the present invention is produced as follows: the sample-receiving parts are formed on the support by a printing technique such as a screen printing or gravure printing by using a solution of the above-described material for the sample-receiving part in a suitable solvent as an ink, and the printed parts are dried (Examples 2 to 6, FIGS. 2 to 7). Techniques usually employed for printing can be employed for the production of the test kit of the present invention. Particularly preferred are screen printing and gravure printing techniques.

The formation of the sample-receiving parts by the printing technique as described above is preferred from the viewpoint of reduction in the cost of the test kit per se by mass production and, in addition, this technique is suitable for forming the minute sample-receiving parts or for forming the sample-receiving parts capable of containing an accurate intended amount of a reagent during the test. This technique is suitable particularly for forming the test kit having parts for retaining a large amount of a sample in automatic tests.

When the sample-receiving parts are formed by printing, the arrangement, shape, thickness, etc. of the sample-receiving parts can be controlled by controlling the shape of the printing plate. It is also possible to form the sample-receiving parts having different thicknesses by single printing operation. When the sample-receiving parts having a desired thickness cannot be formed by the single printing operation, the printing can be repeated on given parts to increase the thickness of these parts.

In another process for producing the test kit of the present invention by the printing technique, diaphragms between the sample-receiving parts are previously formed on the support by printing and then a material for forming the sample-receiving parts is fed into the parts formed on the support and defined by the diaphragms to obtain the test kit.

For example, independent parts to be used for forming the sample-receiving parts are defined on the support made of a suitable material. For instance, a lattice pattern is formed by the above-described printing technique. Then a material for forming the sample-receiving parts, such as a solution of a polymer as described above in a suitable solvent, is poured into the independent parts formed by the pattern and the material is dried to obtain the test kit of the present invention.

A reagent used for a chemical test or microbiological test may be previously contained in the sample-receiving parts of the test kit of the present invention. For example, when the test kit is used for the determination of the antimicrobial susceptibility by the microdilution broth method as described above, a predetermined amount of the antimicrobial drug to be used is previously fed into the sample-receiving parts so that the antimicrobial susceptibility can be easily determined by merely adding a suspension of a predetermined amount of a bacterium in a suitable medium in the test.

When sample-receiving parts each capable of containing the same amount of a medium and having an antimicrobial drug content which varies stepwise are formed in the test kit, the antimicrobial susceptibility can be easily determined by adding equal amounts of a suspension of a given microbial sample in a medium to each sample-receiving part of the test kit and observing the propagation of the microorganism. The antimicrobial drug content varies from one sample-receiving part to another in that there is, for example, a two-fold increase from one to the other for attaining the object of the above-described test.

The reagent used in the test is previously incorporated into the sample-receiving parts as follows: when a fibrous material such as a filter paper or a porous sponge is used for forming the sample-receiving parts, the sample-receiving parts are impregnated with a solution of the reagent and then dried; or when a polymer is used, the reagent is added to a solution or dispersion of the polymer to be applied to the support to easily incorporate the reagent into the sample-receiving parts.

In the latter case, many sample-receiving parts can be easily and efficiently formed on the support by mixing the reagent into a solution or dispersion of the polymer or water-absorbing gel in a solvent, applying the resultant mixture to the support by a printing method and drying it.

In the formation of the sample-receiving parts by the printing, it is possible to form multi-layer sample-receiving parts containing two or more reagents by conducting the printing two or more times with inks each containing a different reagent and a material for forming the sample-receiving parts. It is also possible to form sample-receiving parts each having a different reagent content by repeating the printing with the same ink containing the reagent and the material for forming the sample-receiving parts, the number of times of repetition being various among the sample-receiving parts.

Each of the sample-receiving parts of the test kit of the present invention may comprise a portion for absorbing the sample and a portion for previously containing the reagent (a reagent-containing portion) so that when a sample is added to these two portions at the time of the use, both of these portions function as a sample-receiving part.

In this case, it is possible to form the portion for absorbing the sample on the support by, for example, printing with an ink comprising a water-absorbing gel, a binder and a solvent or dispersing medium and then forming a reagent-containing portion having substantially the same shape as the formerly formed portion for absorbing the sample thereon by printing to form a laminate of the two layers usable as the sample-receiving part. The order of the arrangement of the sample-absorbing portion and the reagent-containing portion on the support may be contrary to the above-described order.

Figure 7:
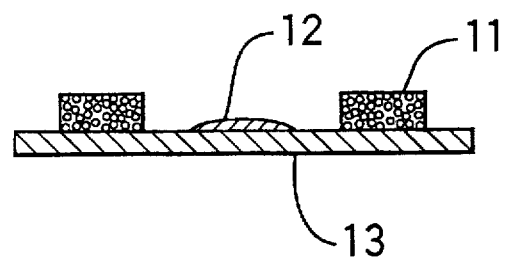
FIG. 7 is a rough cross section of the sample-receiving part of the test kit of the present invention, which comprises a portion for absorbing a sample and a reagent-containing portion. The sample-receiving part shown in FIG. 7 comprises a portion 11 for absorbing the sample which comprises a water-absorbing gel provided on support 13, and a reagent-containing portion 12.
Figure 8:
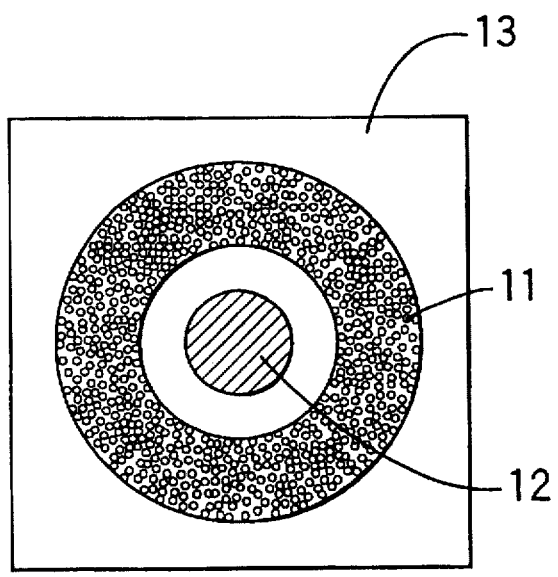
FIG. 8 is a rough plan of the sample-receiving part shown in FIG. 7.

Alternatively, the sample-receiving parts of the test kit of the present invention can comprise a reagent-containing portion and a surrounding portion for absorbing the sample, both portions being independently formed on the support as shown in FIG. 7 (cross section) and FIG. 8 (plan). In this embodiment, the material for forming the sample-absorbing portion can be selected from among materials capable of swelling by absorbing water so that when the sample is added, the sample-absorbing portion is swollen to cover the reagent-containing portion and thereby to form an integral portion so as to spread the reagent to the whole portion. Examples of preferred materials suitable for this purpose include the above-described water-absorbing gels.

Figure 9:
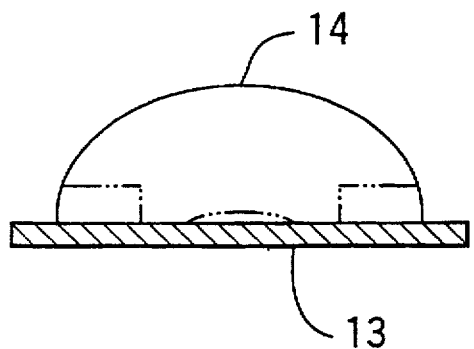
FIG. 9 is a rough cross section of the sample-receiving part shown in FIG. 7 to which a sample is added.

When the sample is added to the sample-receiving part shown in FIG. 7 prepared by using the water-absorbing gel, the water-absorbing gel in the sample-absorbing portion is swollen as shown in FIG. 9 to exhibit a function of the sample-receiving part.

In the sample-receiving part of such a type, the sample-absorbing portion and the reagent-containing portion may be in contact with each other or they may be separated to some extent so far as the two portions can be unified when the sample is added.

Figure 10:
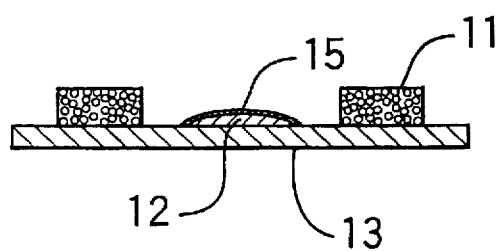
FIG. 10 is a rough cross section showing a modification of the sample-receiving part shown in FIG. 7. The sample-receiving part shown in FIG. 10 has a protecting layer 15 on the reagent-containing portion 12.

When the sample-receiving part as shown in FIG. 7 is formed, a projecting layer made of one of the above-described polymers may be formed over the reagent-containing portion as shown in FIG. 10 so as to protect the reagent from falling off.

When the sample-absorbing portion and the reagent-containing portion are formed separately as described above, the sample-receiving parts each containing a different amount of the reagent while keeping the amount of the sample kept therein constant can be easily formed as follows: the sample-absorbing portion is formed from predetermined amounts of a water-absorbing gel and binder and the reagent-containing portion is formed by printing with an ink comprising the reagent and a binder. In, for example, gravure printing, the amount of the reagent-containing ink is varied by varying the quantity of the transfer by varying the plate depth and number of lines, or the concentration of the reagent is varied.

When the above-described test kit of the present invention is used, a desired reaction solution, culture liquid or the like is fed into the sample-receiving part of the test kit to conduct the reaction, culture or the like and, if necessary, a necessitated reactant is added after the completion of the reaction or culture and the test results are detected from color, luminescence, fluorescent light or change in turbidity according to the principle of the test.

For example, the minimum inhibitory concentration of an antimicrobial drug can be detected by a method wherein the propagation of the bacteria in the mecium is macroscopically detected, a method wherein the turbidity of the medium is determined at an absorbancy of 640 to 660 nm, or a method wherein a fluorescent substrate is incorporated into a medium, a fluorescent substance is formed by a bacterial enzyme which is accumulated in the medium as the bacteria propagate, and the amount of the fluorescent substance is determined by determining the fluorescent intensity.

A reaction liquid or culture liquid is added to the sample-receiving parts usually by measuring such a liquid with a micropipet or the like. However, when the sample-receiving part is capable of absorbing a substantially predetermined amount of a sample when this part is brought into contact with the sample to be contained therein, the whole test kit of the present invention or the sample-receiving parts thereof are immersed in a sample to be kept in the sample-receiving parts and then drawn up, and excess sample is removed.

The easiest method for the evaluation of the test results is the macroscopic observation. When exact results are necessitated or when the results cannot be macroscopically observed since, for example, the sample-receiving parts are particularly minute, the test results can be obtained by detecting the above-described turbidity, color, luminescence or fluorescent light with an ordinary detecting apparatus. In the determination of the absorbance, fluorescent intensity and so on in the determination of the minimum inhibitory concentration of the antimicrobial drug, a commercially available absorptiometer or fluorophotometer can be used. The test kit of the present invention can be designed so that it fits such an automatized known meter.

The test kit of the present invention is usable for various chemical tests and microbiological tests which have been conventionally conducted by use of a plastic microplate in which a biological substance such as an antigen, antibody or enzyme or a non-biological substance such as a coloring compound is used as a sample or reagent. In addition, such a test kit having such a structure as described above can be produced at an extremely low cost with this test kit wherein a necessary reagent is previously kept therein, the tests can be conducted very easily.

The following Examples will further illustrate the present invention, which by no means limit the invention.

EXAMPLE 1

(Example of test kit in which the sample-receiving part is made of a pulp disc)

11 streptomycin-containing pulp discs having a diameter of 8 mm and 2 streptomycin-free control pulp discs were adhered to a rectangular acrylic plate having a size of 17 cm×1 cm×0.5 mm at intervals of 5 mm with a pressure-sensitive adhesive double coated tape. The streptomycin contents of the discs were 1280, 640, 320, 160, 80, 40, 20, 10, 5, 2.5 and 1.25 ng, respectively. A partial rough perspective view of the tester is given in FIG. 1.

Staphylococcus aureus ATCC 25923 was used as the test microorganism. This microorganism was cultured on an agar medium overnight and then suspended in sterilized physiological saline to obtain a suspension of about $10^8$ CFU/ml. The suspension was diluted to a 1/1000 concentration (about $10^5$ CFU/ml) with a Mueller-Hinton broth (comprising 300 g of meat extract, 17.5 g of casamino acid, 1.5 g of starch and 1,000 ml of purified water). 20 μl of the broth containing the test microorganism was added to each of the dry discs fixed on the acrylic plate with a micropiper. For control, the same amount (20 μl) of the microbe-containing broth or the microbe-free broth were added to the drug-free discs (Controls 1 and 2).

The rectangular acrylic plate having the sample-containing discs was placed in a small box saturated with steam to conduct the culture at 35±1° C. for 19 hours. After the completion of the culture, 20 µl of previously prepared 0.0275 wt. % aqueous resazurin solution was dropped into each pulp disc. After leaving the plate to stand for 30 minutes, it was compared with the controls, and MIC was given in terms of the minimum drug concentration of a disc having the same blue color as that of the controls.

In this experiment, MIC was 4 µg/ml.

EXAMPLE 2

(Example wherein a mixture of crystalline cellulose and acacia gum is used as the material for the sample-receiving part)

11 parallel bands having a width of 5 mm and arranged at intervals of 5 mm and comprising a tetracycline-containing mixture of crystalline cellulose and acacia gum were drawn on a transparent polyvinyl chloride plate having a size of 14 cm×14 cm×0.5 mm by using a mixture of 100 ml of water, 30 g of crystalline cellulose, 20 g of acacia gum and tetracycline by screen printing method. The bands were then dried. The thermography was employed so that the thickness of the bands after drying would be about 0.5 mm. The amount of tetracycline in the mixture varied so that the 5 mm bands drawn as described above would have tetracycline contents of 640, 320, 160, 80, 40, 20, 10, 5, 2.5, 1.25 and 0.625 ng, respectively. For control, two bands of the tetracyclin-free mixture were drawn in the same manner as that described above.

Figure 2:
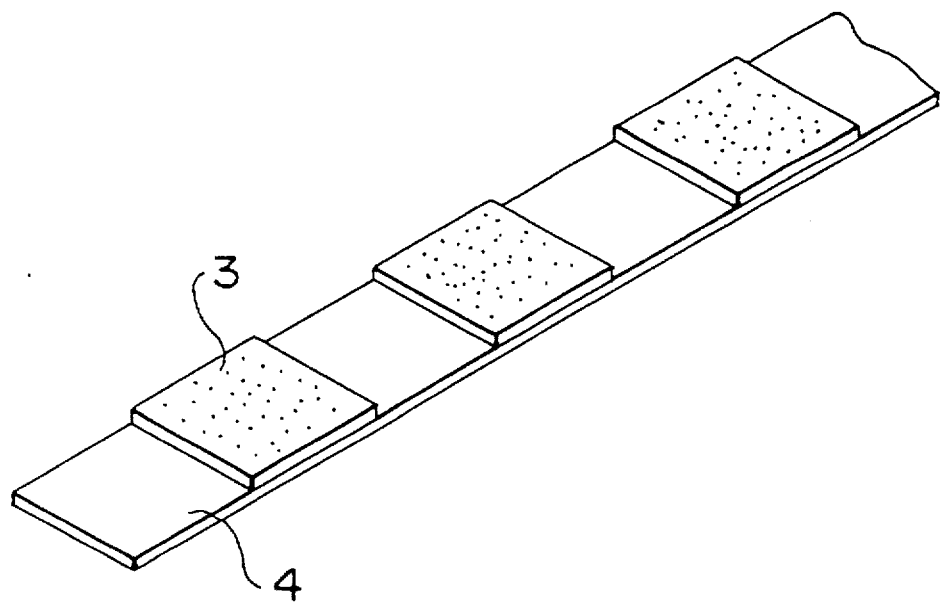
FIG. 2 is a partial rough perspective view of a test kit of the present invention produced in Example 2. The test kit of the present invention produced in Example 2 is composed of sample-receiving parts 3 each comprising crystalline cellulose and acacia gum, and a polyvinyl chloride platy support 4.

After drying, the polylvinyl chloride plate was cut at a right angle to the longitudinal direction into pieces having a width of 5 mm. The test kit of the present invention comprising a rectangular polylvinyl chloride plate having a width of 5 mm and 11 sample-receiving parts (5 mm×5 mm) having the above-described tetracycline content and thickness of about 0.5 mm at intervals of 5 mm and 2 control sample-receiving parts formed thereon was obtained. FIG. 2 is a partial rough perspective view of the test kit thus obtained.

*Escherichia coli* ATCC 25922 was used as the test microorganism. This microorganism was cultured on an agar medium overnight and then suspended in sterilized physiological saline to obtain a suspension of about $10^8$ CFU/ml. The suspension was diluted to a 1/1000 concentration (about $10^5$ CFU/ml) with a Mueller-Hinton broth. 10 µl of the broth containing the test microorganism was added to each of the sample-receiving parts on the rectangular polyvinyl chloride plate with a micropipet. For control, the same amount (10 µl) of the microbe-containing broth or the microbe-free broth were added to the drug-free, sample-receiving parts (Controls 1 and 2).

The rectangular polyvinyl chloride plate having the sample-containing parts was placed in a vessel saturated with steam to conduct the culture at 35±1° C. for 20 hours. After the completion of the culture followed by confirmation that the microorganism grew on the sample-receiving part in Control 1 and that they did not grow on that part in Control 2, MIC was given in terms of the minimum drug concentration in a sample-receiving part in which the growth of the microorganism could not be macroscopically recognized.

In this experiment, MIC was 1 µg/ml.

EXAMPLE 3

(Example wherein polyacrylic acid is used as the material for the sample-receiving parts, and these parts are formed in squares of a lattice formed by screen printing)

A lattice pattern having 12×12 squares (each having a size of 1 cm×1 cm and area of 1 cm$^2$) in it and a line thickness of 5 mm was printed on a polystyrene sheet having a size of 15 cm×15 cm×200 µm by screen printing method by using a solution of an acrylic resin (Dianal BR resin; a product of Mitsubishi Rayon Co., Ltd.) in 50% methyl isobutyl ketone in such a manner that the thickness of the pattern after drying would be 100 µm. The lattice thus formed was then dried.

Figure 3:
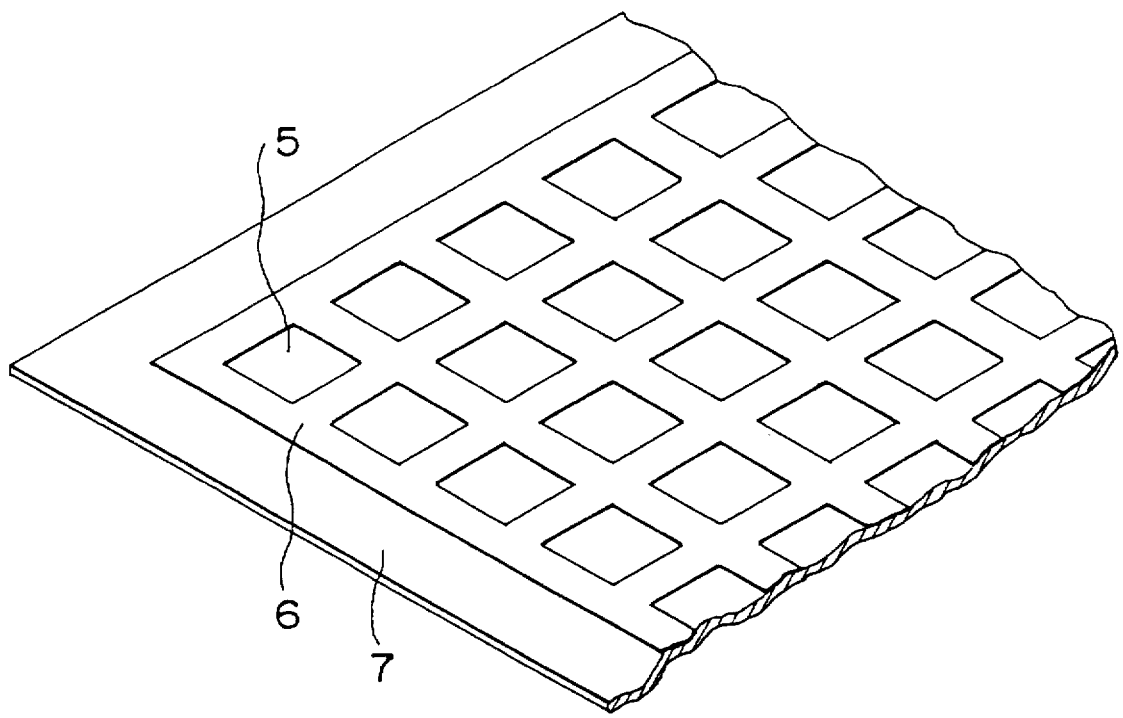
FIG. 3 is a partial rough perspective view of a test kit of the present invention produced in Example 3. The test kit of the present invention produced in Example 3 is composed of sample-receiving parts 5 each comprising polyacrylic acid, a lattice pattern 6 made of an acrylic resin, and a polystyrene sheet 7 as the support.
Figure 4:
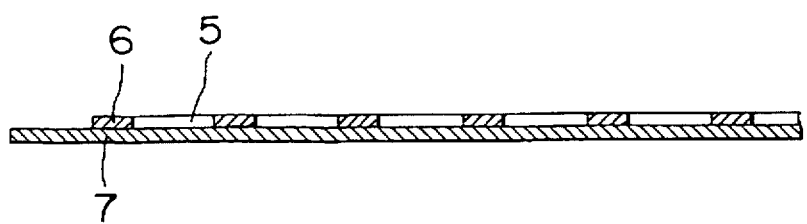
FIG. 4 is a partial rough cross section of the test kit of the present invention produced in Example 3.

10 µl of 50% solution of tetracycline in polyacrylic acid (a product of Junsei Kagaku K. K.) was fed into each square with a dispenser and then dried to form the sample-receiving parts. The amount of tetracycline in the solution varied so that the tetracycline contents in the squares would be 640, 320, 160, 80, 40, 20, 10, 5, 2.5, 1.25 and 0.625 ng, respectively, while the amount of the polyacrylic acid coating would be constant. For control, a lattice containing tetracycline-free polyacrylic acid solution was also formed. FIGS. 3 and 4 are partial rough perspective view and cross section of the test kit thus produced.

*Escherichia coli* ATCC 25922 was used as the test microorganism. This microorganism was cultured on an agar medium overnight and then suspended in sterilized physiological saline to obtain a suspension of about $10^8$ CFU/ml. The suspension was diluted to a 1/1000 concentration (about $10^5$ CFU/ml) with a Mueller-Hinton broth. 10 µl of the broth containing the test microorganism was added to each of the sample-receiving parts with a micropipet. For control, the same amount (10 µl) of the microbe-containing broth or the microbe-free broth was added to the drug-free, sample-receiving parts (Controls 1 and 2).

The polystyrene sheet having the sample-receiving parts filled with the sample was placed in a vessel saturated with steam to conduct the culture at 35±1° C. for 20 hours. After the completion of the culture followed by confirmation that the microorganism grew on the sample-receiving part in Control 1 and that they did not grow on that part in Control 2, MIC was given in terms of the minimum drug concentration in a sample-receiving part in which the growth of the microorganism could not be macroscopically recognized.

In this experiment, MIC was 1 µg/ml.

EXAMPLE 4

(Example wherein gelatin is used as the material for the sample-receiving parts, and these parts are formed by gravure printing method)

A 5% gelatin solution containing 0.04% of tetracycline was prepared. The gelatin solution was continuously applied to a triacetylcellulose film having a width of 10 cm and thickness of 200 µm with a gravure roll in which the cells were so designed that 5 square patterns (0.25 cm$^2$) were printed at longitudinal intervals of 1 cm; the amount of the coating being varied so that there was a twofold increase from one to the other, and the repetition pitch intervals of the groups of 5 square patterns being 1.5 cm. Thus, a series of groups each consisting of 5 square patterns (0.25 cm$^2$) containing 5, 10, 20, 40 and 80 ng, respectively, of tetracycline was continuously formed on the support.

Figure 5:
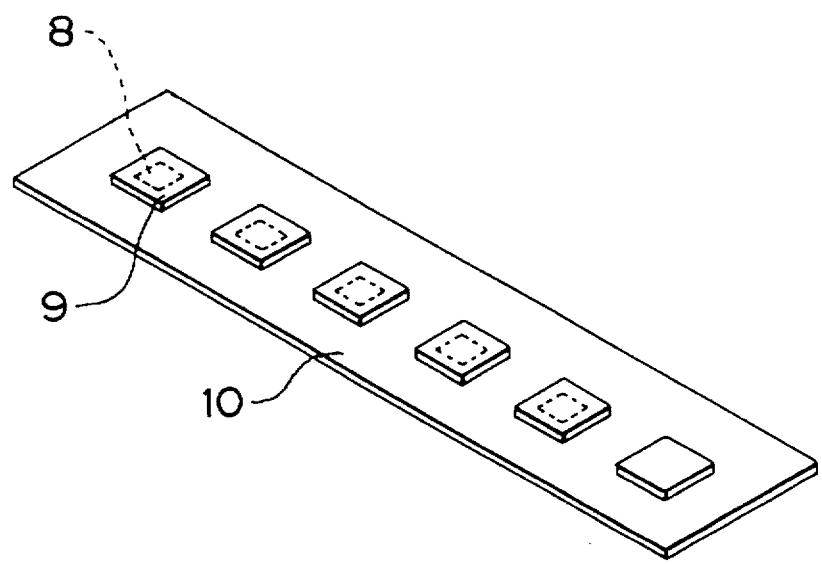
FIG. 5 is a rough perspective view of a test kit of the present invention produced in Example 4. The test kit of the present invention produced in Example 4 comprises tetracycline-containing gelatin 8, 1 cm$^2$ gelatin coating 9 and triacetylcellulose support 10.
Figure 6:
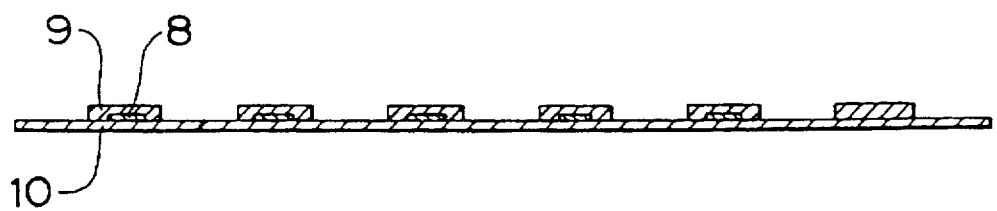
FIG. 6 is a rough cross section of the test kit of the present invention produced in Example 4.

Then a 1 cm$^2$ coating was formed on each of the small parts with 30% gelatin solution so that 200 ng/cm$^2$ of gelatin would be applied thereto. For control, a tetracycline-free coating having the same shape in the same amount as those described above was continuously formed beside the group consisting of the 5 square patterns containing tetracycline in the same manner as above. Then the film thus having a series of the group of 6 square patterns was transversely cut at a portion between the groups to obtain the rectangular test kits of the present invention each having a size of 1.5 cm×10 cm and also having 6 square patterns. FIGS. 5 and 6 are rough perspective view and cross section of the test kit.

The test kit of the present invention produced as described above has both sample-receiving parts containing the tetracycline-containing gelatin and sample-receiving part containing the tetracycline-free gelatin. When a culture liquid is added to the sample-receiving parts, tetracycline diffuses over the whole sample-receiving parts to obtain intended tetracycline contents.

*Escherichia coli* ATCC 25922 was used as the test microorganism. This microorganism was cultured on an agar medium overnight and then suspended in sterilized physiological saline to obtain a suspension of about $10^8$ CFU/ml. The suspension was diluted to a 1/1000 concentration (about $10^5$ ,CFU/ml) with a Mueller-Hinton broth. The sheet produced as described above and having the tetracycline-containing sample-receiving parts and tetracycline-free sample receiving part was immersed in the suspension for several seconds so that the sheet absorbed the microbe-containing broth.

The test kit having the sample-receiving parts filled with the sample was placed in a vessel saturated with steam to conduct the culture at 35±1° C. for 20 hours. After the completion of the culture followed by confirmation that the microorganism grew on the sample-receiving part in Control 1 and that they did not grow on a control sample-receiving part obtained by immersing the sheet in a microbe-free broth in the same manner as above, MIC was given in terms of the minimum drug concentration in a sample-receiving part in which the growth of the microorganism could not be macroscopically recognized.

In this experiment, MIC was 1 μg/ml.

EXAMPLE 5

(Example wherein the sample-receiving part is composed of a portion for receiving sample and a portion containing a reagent, and a water-absorbing gel is used for forming the sample-receiving portion)

8×8 circular patterns having an inner diameter of 7 mm, outer diameter of 9 mm and frame width of 1 mm were formed on a polyethylene terephthalate sheet having a size of 20 cm×20 cm×125 μm with an ink prepared by dispersing 30 g of a water-absorbing gel (Sumika Gel; a product of Sumitomo Chemical Co., Ltd.) in a solution of 56 g of an acrylic resin (Sericol Medium; a product of Teikoku Ink Seizo K. K.) in 14 g of cyclohexanone by screen printing method so that the thickness after drying would be 70 μm, and then dried.

10 μg of a 5% solution of an antimicrobial drug selected from among piperacillin sodium (PIPC), methylphenylisoxazolylpenicillin sodium (MPIPC), cefazolin sodium (CEZ), cefmetazole sodium (CMZ), ceftizoxime sodium (CZX), minocycline hydrochloride (MINO) and ofloxacin (OFLX) in hydroxypropylcellulose (a product of Nippon Soda Co., Ltd.) was poured in each of the circular patterns with a dispenser.

For control, a pattern filled with the antimicrobial drug-free hydroxypropylcellulose solution was also formed.

*S. aureus* ATCC 25923 was used as the test microorganism. This microorganism was cultured on an agar medium overnight and then suspended in sterilized physiological saline to obtain a suspension of about $10^8$ CFU/ml. The suspension was diluted to a 1/1000 concentration (about $10^5$ CFU/ml) with a Mueller-Hinton broth. 50 μl of the broth containing the test microorganism was dropped into each pattern with a micropipet. For control, the same amount (50 μl) of the microbe-containing broth or the microbe-free broth was dropped into the drug-free patterns.

The sheet having the sample-receiving parts filled with the sample was placed in a plastic vessel saturated with steam to conduct the culture at 35±1° C. for 16 to 18 hours.

After the completion of the culture, MIC was given in terms of the minimum drug concentration in a sample-receiving part in which the growth of the microorganism could not be macroscopically recognized.

MIC values obtained in this Example are given in the following Table 1, wherein MIC values determined by an ordinary microdilution broth method are also given in addition to MIC values determined with the test kit of the present invention produced as described above.

TABLE 1

| Antimicrobial drug | Tester of the present invention (n = 3) | Microdilution broth method (n = 5) |
|---|---|---|
| PIPC | 0.5 | 0.5 |
| MPIPC | 0.25 | 0.25 |
| CEZ | 0.5 | 0.5 |
| CMZ | 1.0 | 1.0 |
| CZX | 1.0 | 1.0 |
| MINO | 0.25 | 0.25 |
| OFLX | 0.5 | 0.5 | n represents the number of times of the determination, and the numerals represent the average values.

EXAMPLE 6

(Example wherein the sample-receiving part is composed of a sample-receiving portion and a reagent-containing portion, and a water-absorbing gel is used as the material for the sample-receiving part)

A 5% solution of hydroxypropylcellulose (Nippon Soda Co., Ltd.) containing 0.08% of antimicrobial PIPC, CEZ, erythromycin (EM), MINO or OFLX as shown in the following Table 2 was prepared. The hydroxypropylcellulose solution was applied to a polyethylene terephthalate sheet having a size of 20 cm×20 cm×125 μm in a gradational manner so that a series of groups each consisting of 8 circular patterns having an inner diameter of 4 mm and containing 100, 50, 25, 12.5, 6.25 and 3.125 ng of the antimicrobial drug given in Table 2 was continuously formed on the support with a gravure plate in which the cells were so designed that 8 circular patterns having a diameter of 4 mm were continuously printed at longitudinal intervals of 1.9 cm; the amount being varied so that there was a two-fold increase from one to the other, and the repetition pitch intervals being 1.7 cm.

8×8 circular patterns having an inner diameter of 7 mm, outer diameter of 9 mm and frame width of 1 mm were formed by the screen printing method in the same manner as that of Example 5 with an ink prepared by dissolving 16.8 g of hydroxypropylcellulose (HPC) or polyvinylpyrrolidone (PVP; a product of Junsei Kagaku K. K.) as the water-soluble resin in 6 g of n-butanol, adding 20 g of cyclohexanone to the obtained solution and dispersing 30 g of a water-absorbing gel (Diawet; a product of Mitsubishi Petrochemical Co., Ltd.) in such a manner that each pattern would surround the above-described small portion so that the thickness after drying would be 50 μm, and then dried.

*Staphylococcus aureus* ATCC 25923, *Staphylococcus epidermidis* ATCC 12228 or *Klebsiella pneumoniae* ATCC 10031 were used as the test microorganisms. These microorganisms were cultured on an agar medium overnight and then suspended in sterilized physiological saline to obtain suspensions of about $10^8$ CFU/ml. Each of the suspensions was diluted to a 1/1000 concentration (about $10^5$ CFU/ml) with a Mueller-Hinton broth. 50 μl of the broth containing the test microorganism was dropped into each pattern with a micropipet. For control, the same amount (50 μl) of the microbe-containing broth or the microbe-free broth was dropped into the drug-free patterns.

The sheet having the sample-receiving parts filled with the sample was placed in a plastic vessel saturated with steam to conduct the culture at 35±1° C. for 16 to 18 hours. After the completion of the culture, MIC was given in terms of the minimum drug concentration in a sample-receiving part in which the growth of the microorganism could not be macroscopically recognized.

MIC values obtained in this Example are given in the following Table 2, wherein MIC values determined by an ordinary microdilution broth method are also given in addition to MIC values determined with the test kit of the present invention produced as described above.

TABLE 2

| Microorganism | Determination method | | Antimicrobial drug | | | | |
|---|---|---|---|---|---|---|---|
| | | | PIPC | CEZ | EM | MINO | OFLX |
| S. aureus | microdilution broth | | 0.5 | 0.5 | 0.25 | 0.25 | 0.5 |
| ATCC 25923 | kit of the invention | (HPC) | 0.5 | 0.5 | 0.25 | 0.125 | 0.5 |
| | kit of the invention | (PVP) | 0.5 | 0.5 | 0.25 | 0.125 | 0.5 |
| S. epidermidis | microdilution broth | | >2.0 | 0.5 | 0.25 | 0.25 | 0.5 |
| ATCC 12228 | kit of the invention | (HPC) | >2.0 | 0.5 | 0.25 | 0.25 | 0.5 |
| | kit of the invention | (PVP) | >2.0 | 0.5 | 0.25 | 0.25 | 0.5 |
| S. pneumoniae | microdilution broth | | >2.0 | 2.0 | >2.0 | 0.25 | 0.06 |
| ATCC 10031 | kit of the invention | (HPC) | >2.0 | 2.0 | 2.0 | 0.125 | ≦0.06 |
| | kit of the invention | (PVP) | >2.0 | 2.0 | 2.0 | 0.25 | ≦0.06 |

The number of times of determination was 3 in the microdilution method and 2 when the test kit of the invention was used. The numerals represent the average values.

What is claimed is:

1. A test kit for a chemical test or microbiological test, comprises (a) a platelike support of hydrophobic material (b) one or more independent sample-receiving parts each comprising (I) a part comprising a first hydrophilic, water absorbing material for absorbing a sample and a reagent for the chemical test or microbiological test and (II) a surrounding part comprising a second hydrophilic, water-absorbing material, which may or may not be the same as the first material, comprising a gel, said gel having water-absorbing, hydrophilic and water-retaining properties, which surrounds the part (I), is separated from the part (I), and prevents escape of the sample.

2. The test kit according to claim 1, wherein the materials of the sample receiving parts are applied by printing on said support resulting in a plurality of adjacent sample receiving parts, the area of the sample-receiving part is about 5 mm$^2$, the intervals between the adjacent sample-receiving parts are about 0.5 mm, and the thickness of the sample receiving parts are about 0.01 to 500 μm.

3. The test kit according to claim 1, wherein the material having water absorbing, hydrophilic and water retaining properties is selected from the group consisting of a polyvinyl alcohol/polyacrylate gel, crosslinked polyacrylate gel, crosslinked polyvinyl alcohol gel, crosslinked polyethylene oxide gel, crosslinked polydiethylacrylamide gel, cross linked polyisoproylacrylacide gel, crosslinked polyvinylpyrrolidone gel, crosslinked Paogen gel and mixtures thereof.

4. The test kit according to claim 1, wherein the material having water-absorbing, hydrophilic and water-retaining properties is selected from the group consisting of starch, agar, pullulan, casein, gelatin, crystalline cellulose, methylcellulose, ethylcellulose, carboxymethylcellulose, hydroxyethylcellulose, hydroxypropylcellulose, polyvinyl alcohol, polyethylene glycol, polypropylene glycol, polyacrylamide, polyacrylic acid, sodium polyacrylate, polyvinylpyrrolidone, Paogen, copolymers obtained by copolymerizing such a polymer with another monomer, acacia gum and mixtures thereof.

5. The test kit according to claim 4, wherein the material having water-absorbing, hydrophilic and water-retaining properties is selected from the group consisting of polyvinylpyrrolidone, hydroxyethylcellulose, hydroxypropylcellulose, polyethylene glycol, polyvinyl alcohol, Paogen and mixtures thereof.

6. The test kit according to claim 1, wherein the material having water-absorbing, hydrophilic and water-retaining properties, which forms the part (I), is selected from the group consisting of filter papers, pulp discs and spongy porous substances.

7. The test kit according to claim 6 wherein the surrounding part (II) has a circular shape having a diameter of about 3 to 20 mm or a rectangular shape having a side length of about 3 to 20 mm, and the thickness of the part being 0.5 to 3 mm.

8. The test kit according to claim 6, wherein the amount of a sample to be fed into each sample-receiving part is 0.005 to 0.1 ml.

9. The test kit according to claim 1, wherein the sample-receiving part contains a reagent for a chemical test or microbiological test.

10. The test kit according to claim 9, which has two or more sample-receiving parts each containing a different amount of a reagent.

11. The test kit according to claim 9, which has two or more sample-receiving parts each containing a different reagent.

12. The test kit according to claim 9, which is for the determination of antimicrobial susceptivility by a microdilution broth method.

13. The test kit according to claim 12, which has two or more sample-receiving parts containing antimicrobial drug in a gradationally changing amount.

* * * * *